(12) United States Patent
Li et al.

(10) Patent No.: US 8,809,620 B2
(45) Date of Patent: Aug. 19, 2014

(54) HEPARANASE DEFICIENT NON-HUMAN MAMMALS

(75) Inventors: Jin-ping Li, Uppsala (SE); Ulf Lindahl, Uppsala (SE); Israel Vlodavsky, Mevasseret Zion (IL); Eyal Zcharia, Jerusalem (IL)

(73) Assignee: Shenzhen Hepalink Pharmaceutical Co., Ltd., Shenzhen (CN)

( * ) Notice: Subject to any disclaimer, the term of this patent is extended or adjusted under 35 U.S.C. 154(b) by 702 days.

(21) Appl. No.: 12/937,091

(22) PCT Filed: Apr. 9, 2009

(86) PCT No.: PCT/IB2009/051506
§ 371 (c)(1),
(2), (4) Date: Feb. 28, 2011

(87) PCT Pub. No.: WO2009/125369
PCT Pub. Date: Oct. 15, 2009

(65) Prior Publication Data
US 2011/0154511 A1 Jun. 23, 2011

(30) Foreign Application Priority Data

Apr. 11, 2008 (FI) .................................... 20085308

(51) Int. Cl.
*A01K 67/027* (2006.01)
*A01K 67/02* (2006.01)

(52) U.S. Cl.
USPC ............................................. 800/18; 800/21

(58) Field of Classification Search
USPC ..................................................... 800/18, 21
See application file for complete search history.

(56) References Cited

U.S. PATENT DOCUMENTS

| 6,503,712 B1 * | 1/2003 | Thukral ........................ 506/14 |
| 2002/0168749 A1 | 11/2002 | Pecker et al. |
| 2003/0190737 A1 * | 10/2003 | Pecker et al. ................ 435/200 |
| 2005/0137167 A1 * | 6/2005 | Casu et al. .................... 514/56 |

OTHER PUBLICATIONS

Li and Lindahl (2007) "GLYCO 19 International Symposium on Glycoconjugates: Abstracts" Glycoconjugate Journal, vol. 24, (6-7), 259-407, abstract 026.*
LePage et al. (2006) Methods in Molecular Medicine, vol. 129, 41-67.*
"Hypercholesterolemic mice:liver-specific PCSK9 knockout" flintbox, posted Jan. 14, 2008, http://www.flintbox.com/public/project/2027.*
Clark et al. (2003) Nature Reviews: Genetics. vol. 4, 825-833.*
Niemann et al (2005) Rev. Sci, Tech. Off. Int. Spiz. vol. (24), 285-298.*
Wheeler (2001) Theriogenology. vol. 56, 1345-1369.*
Prelle et al. (2002) Anat. Histol. Embryol., vol. 31, 169-186.*
Boyd et al. (2004) J. Nat. Canc. Inst., vol. 96(16), 1194-1195.*
Boyd et al., "Involvement of Heparanase in Tumor Metastases: A New Target in Cancer Therapy?" Journal of the National Cancer Institute (Aug. 18, 2004) vol. 96, No. 16, pp. 1194-1195.
European Search Report issued Jun. 14, 2011, in European Patent Application No. 09730364.8.
GLYCO 19 International Symposium on Glycoconjugates: Abstracts, Glycoconjugate Journal (Jun. 29, 2007) vol. 24, No. 6-7, pp. 259-407.
Ilan et al., "Regulation, function and clinical significance of heparanase in cancer metastasis and angiogenesis," The International Journal of Bichemistry & Cell Biology (2006) vol. 38, pp. 2018-2039.
van den Hoven et al., "Heparanase in glomerular diseases," Kidney International (2007), vol. 72, No. 5, pp. 543-548.
Zcharia et al., "Newly Generated Heparanase Knock-Out Mice Unravel Co-Regulation of Heparanase and Matrix Metalloproteinases," PLoS ONE (Apr. 2009) vol. 4, No. 4, pp. 1-13.

* cited by examiner

*Primary Examiner* — Anne Marie S Wehbe
(74) *Attorney, Agent, or Firm* — Birch, Stewart, Kolasch & Birch, LLP

(57) ABSTRACT

The invention relates to cells and transgenic non-human mammals having at least one disrupted heparanase allele. The invention further relates to methods of screening therapeutic drug candidates utilizing the heparanase deficient non-human mammals and cells.

12 Claims, 8 Drawing Sheets

SEQUENCE LISTING

<160> NUMBER OF SEQ ID NOS: 29

<210> SEQ ID NO 1
<211> LENGTH: 3253
<212> TYPE: DNA
<213> ORGANISM: Mus musculus

<400> SEQUENCE: 1
aagcttcctc aagggactg caaagcagca gagacaggct gccatctgct tggccttgta      60
cacctgagtt cagctagcgc tgatgcttgg gcagattggt gtgtgtgagt gtgtgtgtgt     120

-continued

```
gtgtgtgtgt gtgtgtgtgt agcatggttc aagcttcttt catggtaaca cacacacaca      180
cacacacaca cacacacaca caagcttcag cacttgtttg ctatcattat ataccagtgt      240
aaaatgtcaa gggaaaacaa aagttgcagc aaccgcaaaa gatgggtttg ggggaggggt      300
tgctcaggat tccaagggta gttgcttggg ggcttcttgc tgggttttag cggttggcca      360
agcctcagag caactcttag gcaggctctc ccaaatactg ttttcataat actgctttaa      420
aaacagggtc cccaccacca tcaccaccac ccccgtgcaa ggaccgattt ctagttgcat      480
tttagccaat gctcggatca ggttttcaa gcgacaaaga gatacctgag atcctgggca      540
gaggacatcc tagctcggtc agatttgggc aggctcaagt gaccagtgtc ttaaggcaga      600
agggagtcgg ggtagggtct ggctgaaccc tcaaccgggg cttttaactc agggtctagt      660
cctggcgcca aatggatggg acctagaaaa ggtgacagag tgcgcaggac accaggaagc      720
tggtcccacc cctgcgcggc tcccgggcgc tccctcccca ggcctccgag gatcttggat      780
tctggccacc tccgcaccct ttggatgggt gtggatgatt tcaaaagtgg acgtgaccgc      840
ggcggagggg aaagccagca cggaaatgaa agagagcgag gaggggaggg cggggagggg      900
agggcgctag ggagggactc ccgggagggg tgggagggat ggagcgctgt gggagggtac      960
tgagtcctgg cgccagaggc gaagcaggac cggttgcagg gggcttgagc cagcgcgccg     1020
gctgccccag ctctcccggc agcgggcggt ccagccaggt gggatgctga ggctgctgct     1080
gctgtggctc tggggccgc tcggtgccct ggcccagggc gccccgcgg ggaccgcgcc      1140 gaccgacgac gtggtagact tggagtttta caccaagcgg ccgctccgaa gcgtgagtcc     1200
ctcgttcctg tccatcacca tcgacgccag cctggccacc gacccgcgct tcctcacctt     1260
cctggggtaa gtgcagcccc taggttctgt cccttcgtct gtcctcggct ccccctcgcc     1320
tgtccaatca cactcgcgag ggccagccac tctcttcgct caaacaactt tgtgtttgct     1380
ctctggagcc tccctcctgt gtgcactcac ccctcaaaag acttttcctg attcatttac     1440
tcagcgcttg ttgcctgggc accagccagg tccaggtatg aagtggaaat ttggaggaaa     1500
acaaaaacaa aacaaacgaa gctgtcataa accttagcac tttgtctgga gcctttgaat     1560
tttgcttcag tgtaagacca gtaagctggt gtcccttaaa ctctgttagg aagttttgat     1620
ttaaaagagg aagaaagaaa agataggaaa agcctctatg gagaagaacc attattcatc     1680
ttgctgcctt ttaagcattt aaacattact gggctgggtg tgatacagtt aatgactgt      1740 gtacctcgca tgcaagaaga cctgcatcca tccccagagc tgtgtaatcc ctggcatggg     1800
cacacacttg cagactggca cttgggaagt aggtgtagga ggatcaggag ttaacgcga      1860 tctttagcaa cgtagcaagt ttgagggtag actggactga ataggagtgg agggaggaga     1920
gagagagatg gagaaaggag ccggagactg actgactgac tgactgggaa aatgatagag     1980
gtcagtggga cagacaggag agaatatgac caaaaataca ctttatacac atttgaagat     2040
gtcgtgacga aacccatta ttatgtataa ttaatatatg ctaataaaaa caccatagag      2100
gcacgattct ccaagatgag ggtgcagagc ggaggctgcc tcatcaactg caggaaccac     2160
atctctggcc cctgttccgt gagtgcagac tgtccccaag atgaaaggct caggcacagt     2220
cataggcctt ctaaacttgg gagcctccag agatgaccac gtcctttgtt gtttttgaca     2280
ttgtgtaacc actattgaag gctgaccttg aacttttgat ctccctgcct cttgagggcc     2340
accacactca gctgactaca tcttcaccag cccattctgt caccattgtc aaaggcctag     2400
acttcgatcg catgtccaag cccacactat ctggcatcac tgcagatctc acacagattc     2460
atccccatgg ctaagggtct ggtagtccaa ctaccctgtt ttctccaatc tgactcattg     2520
```

```
gatttctgta atggcttgag agagttggtg cttcttacaa agcttgaagg ttaagctaat    2580
tgtttcgtct tgcctagcat acacaaaatc ctgggtttca tccacaacat tttgtaaaac    2640
gaggcatggt ggctcatgac ctccacccca gcatttagga gccaaagacg taaggatcag    2700
cagttcaagg ctatcctcgg ctacatagca aggccgggt  gagctgcagc agacgttatc    2760
ttaaaaaaag aaagaaaag  aaagaaaaat gtaaggtct  gttgtgatgg tggacgcgtt    2820
taagcccagc atctgggagg caacgatgaa gaaagtaagg ttgtggggaa ttaaataact    2880
catctgtgac ccatcagcta gtaaatagaa gtagtctttg aagccagact ctgatcacaa    2940
aaacaaaggc ataccaaaag acaacaaact aattattatt tttaaaggaa atagggctgt    3000
gtgtgtgtgt gtgtgtttta aattgcctag aaacaaattg atagactgat taaaaacaac    3060
aacctccatt aacattcagc tagacttggg gcgcaggcct ctgacgtgcc tccaaggagg    3120
tttcaccaga tgaactcgga ggtatgagtt tattacaagc actggaagaa tggaaacagg    3180
tctctctgtc acatttgtaa ccagagaaca gacaatacgc aaaatttaaa tgttaatcat    3240
agaagactct aga                                                       3253
```

<210> SEQ ID NO 2
<211> LENGTH: 20
<212> TYPE: DNA
<213> ORGANISM: Artificial
<220> FEATURE:
<223> OTHER INFORMATION: Primer

<400> SEQUENCE: 2
cgaccgacga cgtggtagac                                                  20

<210> SEQ ID NO 3
<211> LENGTH: 19
<212> TYPE: DNA
<213> ORGANISM: Artificial
<220> FEATURE:
<223> OTHER INFORMATION: Primer

<400> SEQUENCE: 3
gcaacagctc ctggaaggg                                                   19

<210> SEQ ID NO 4
<211> LENGTH: 21
<212> TYPE: DNA
<213> ORGANISM: Artificial
<220> FEATURE:
<223> OTHER INFORMATION: Primer

<400> SEQUENCE: 4
tttctgagct ctgatgcgct g                                                21

<210> SEQ ID NO 5
<211> LENGTH: 21
<212> TYPE: DNA
<213> ORGANISM: Artificial
<220> FEATURE:
<223> OTHER INFORMATION: Primer

<400> SEQUENCE: 5
tgggcctttc actcttgaca g                                                21

<210> SEQ ID NO 6
<211> LENGTH: 20
<212> TYPE: DNA

```
<213> ORGANISM: Artificial
<220> FEATURE:
<223> OTHER INFORMATION: Primer

<400> SEQUENCE: 6
acttgaaggt accgcctccg                                          20

<210> SEQ ID NO 7
<211> LENGTH: 20
<212> TYPE: DNA
<213> ORGANISM: Artificial
<220> FEATURE:
<223> OTHER INFORMATION: Primer

<400> SEQUENCE: 7
gaagctctgg aactcggcaa                                          20

<210> SEQ ID NO 8
<211> LENGTH: 20
<212> TYPE: DNA
<213> ORGANISM: Artificial
<220> FEATURE:
<223> OTHER INFORMATION: Primer

<400> SEQUENCE: 8
atgccaactc tcgtcaacag                                          20

<210> SEQ ID NO 9
<211> LENGTH: 18
<212> TYPE: DNA
<213> ORGANISM: Artificial
<220> FEATURE:
<223> OTHER INFORMATION: Primer

<400> SEQUENCE: 9
gcgctttcgt gcttcctt                                            18

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
agcgtgaagt ttggaagcat                                          20

<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11
cacatccttc acctggtgtg                                          20

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
agacgacata gacggcatcc                                          20
```

```
<210> SEQ ID NO 13
<211> LENGTH: 20
<212> TYPE: DNA
<213> ORGANISM: Artificial
<220> FEATURE:
<223> OTHER INFORMATION: Primer

<400> SEQUENCE: 13
gtggttcagt tgtggtggtg                                                   20

<210> SEQ ID NO 14
<211> LENGTH: 19
<212> TYPE: DNA
<213> ORGANISM: Artificial
<220> FEATURE:
<223> OTHER INFORMATION: Primer

<400> SEQUENCE: 14
gcctggaaca ttctaacga                                                    19

<210> SEQ ID NO 15
<211> LENGTH: 20
<212> TYPE: DNA
<213> ORGANISM: Artificial
<220> FEATURE:
<223> OTHER INFORMATION: Primer

<400> SEQUENCE: 15
ctttgtgggt gaccctgact                                                   20

<210> SEQ ID NO 16
<211> LENGTH: 20
<212> TYPE: DNA
<213> ORGANISM: Artificial
<220> FEATURE:
<223> OTHER INFORMATION: Primer

<400> SEQUENCE: 16
gctgactcgc tatggctacc                                                   20

<210> SEQ ID NO 17
<211> LENGTH: 20
<212> TYPE: DNA
<213> ORGANISM: Artificial
<220> FEATURE:
<223> OTHER INFORMATION: Primer

<400> SEQUENCE: 17
gtcattgggt ccatttgtcc                                                   20

<210> SEQ ID NO 18
<211> LENGTH: 18
<212> TYPE: DNA
<213> ORGANISM: Artificial
<220> FEATURE:
<223> OTHER INFORMATION: Primer

<400> SEQUENCE: 18
atgctccccg ggctgtat                                                     18

<210> SEQ ID NO 19
<211> LENGTH: 24
<212> TYPE: DNA
<213> ORGANISM: Artificial
<220> FEATURE:
```

```
<223> OTHER INFORMATION: Primer

<400> SEQUENCE: 19
cataggagtc cttctgaccc attc                                          24

<210> SEQ ID NO 20
<211> LENGTH: 22
<212> TYPE: DNA
<213> ORGANISM: Artificial
<220> FEATURE:
<223> OTHER INFORMATION: Primer

<400> SEQUENCE: 20
taccttcatt gcacaaacac tg                                            22

<210> SEQ ID NO 21
<211> LENGTH: 22
<212> TYPE: DNA
<213> ORGANISM: Artificial
<220> FEATURE:
<223> OTHER INFORMATION: Primer

<400> SEQUENCE: 21
acttggtgac attatggagg tt                                            22

<210> SEQ ID NO 22
<211> LENGTH: 19
<212> TYPE: DNA
<213> ORGANISM: Artificial
<220> FEATURE:
<223> OTHER INFORMATION: Primer

<400> SEQUENCE: 22
gcggcggtca cagctactt                                                19

<210> SEQ ID NO 23
<211> LENGTH: 23
<212> TYPE: DNA
<213> ORGANISM: Artificial
<220> FEATURE:
<223> OTHER INFORMATION: Primer

<400> SEQUENCE: 23
cacgctcttc agactttggt tct                                           23

<210> SEQ ID NO 24
<211> LENGTH: 22
<212> TYPE: DNA
<213> ORGANISM: Artificial
<220> FEATURE:
<223> OTHER INFORMATION: Primer

<400> SEQUENCE: 24
cctggagacc tgagaaccaa tc                                            22

<210> SEQ ID NO 25
<211> LENGTH: 21
<212> TYPE: DNA
<213> ORGANISM: Artificial
<220> FEATURE:
<223> OTHER INFORMATION: Primer

<400> SEQUENCE: 25
ccacccgagt gtaaccatag c                                             21
```

```
<210> SEQ ID NO 26
<211> LENGTH: 24
<212> TYPE: DNA
<213> ORGANISM: Artificial
<220> FEATURE:
<223> OTHER INFORMATION: Primer

<400> SEQUENCE: 26
cgctacgcca tccagggtct caaa                                              24

<210> SEQ ID NO 27
<211> LENGTH: 24
<212> TYPE: DNA
<213> ORGANISM: Artificial
<220> FEATURE:
<223> OTHER INFORMATION: Primer

<400> SEQUENCE: 27
cggtcatcat cgggcagcac aaaa                                              24

<210> SEQ ID NO 28
<211> LENGTH: 20
<212> TYPE: DNA
<213> ORGANISM: Artificial
<220> FEATURE:
<223> OTHER INFORMATION: Primer

<400> SEQUENCE: 28
agttgctgtc cagcctcagt                                                   20

<210> SEQ ID NO 29
<211> LENGTH: 20
<212> TYPE: DNA
<213> ORGANISM: Artificial
<220> FEATURE:
<223> OTHER INFORMATION: Primer

<400> SEQUENCE: 29
ccaaagtctc ctgccttctg                                                   20
```

HEPARANASE DEFICIENT NON-HUMAN MAMMALS

FIELD OF THE INVENTION

The invention relates to cells and transgenic non-human mammals having at least one disrupted heparanase allele. The invention further relates to methods of screening therapeutic drug candidates utilizing heparanase deficient non-human mammals.

BACKGROUND OF THE INVENTION

Heparanase is a mammalian endo-β-D-glucuronidase that specifically degrades heparan sulfate (HS) proteoglycans ubiquitously associated with cell surfaces and the extracellular matrix. Heparanase activity has been correlated and causally associated with the metastatic potential of tumor-derived cells, attributed to enhanced cell dissemination as a consequence of HS cleavage and remodeling of the ECM barrier. Similarly, heparanase activity is implicated in neovascularization, inflammation and autoimmunity, involving migration of vascular endothelial cells and activated cells of the immune system. Moreover, heparanase upregulation correlates with increased tumor vascularity and poor post-operative survival of cancer patients.

Despite earlier reports on the existence of several mammalian heparin/HS degrading endoglycosidases, cloning of the same gene by several groups indicates that mammalian cells express primarily a single dominant functional heparanase (Hulett et al., Nat. Med., 1999, 5: 803-809; Vlodaysky et al., Nat. Med., 1999, 5: 793-802).

As heparanase plays a critical role in fundamental biological phenomena, ranging from morphogenesis, development and homeostasis to inflammation, angiogenesis and cancer metastasis, there is a need in the art for animal models, which allow studying heparanase in vivo. US patent publication US 2002/0194625 discloses transgenic mice over-expressing human heparanase and uses thereof in studying pathological processes such as tumorigenesis. International patent publication WO 2004/006949 discloses the use of heparanase over-expressing transgenic mice as a model system for testing the role of heparanase in various aspects of hair growth.

Given the important and multifaceted roles of heparanase, animals lacking heparanase activity would provide valuable tools for elaborating the roles of heparanase. Despite of the recognized need in the art and several attempts to create heparanase knockout animals, such animals are not currently available. International patent publication WO 2005/118808 discloses silencing of heparanase activity in cells by small interfering RNA (siRNA) technique. Unfortunately, siRNA technique is not suitable for creating stable knockout mammal lines nor silencing heparanase activity completely.

Thus, animals lacking heparanase activity are still needed.

BRIEF DESCRIPTION OF THE INVENTION

The present invention provides a transgenic non-human mammal having at least one disrupted heparanase allele. In one embodiment, the disrupted heparanase allele lacks promoter and exon 1. More specifically, the disrupted heparanase gene may lack Hind III-XbaI fragment. Said mammals may be heterozygous or homozygous for the disruption.

The present invention also provides isolated cells derived from the above transgenic non-human mammals.

Furthermore, the present invention provides a method of making transgenic non-human mammals having at least one disrupted heparanase allele, the method comprising the steps of deleting part of the heparanase gene by homologous recombination in non-human mammalian embryonic stem cells; introducing recombinant cells obtained into an isolated blastocyst; transplanting said blastocyst into a pseudopregnant non-human mammal; allowing said transplanted blastocyst to develop into a transgenic non-human mammal; breeding said transgenic non-human mammal to produce offspring; and screening said offspring to identify a transgenic non-human mammal having at least one disrupted heparanase allele. In one specific embodiment, the deleted part of the heparanase gene comprises a nucleotide sequence depicted in SEQ ID NO:1.

The present invention also provides vectors comprising a nucleic acid sequence encoding a heparanase knockout construct, wherein at least a portion of one exon of the heparanase coding sequence is replaced with a selectable marker sequence. In one specific embodiment, said selectable marker sequence comprises a neomycin resistance gene.

Moreover, the present invention provides a method of screening a therapeutic drug candidate, comprising the steps of providing a transgenic non-human mammal having at least one disrupted heparanase allele; exposing said mammal to a disease stimulus; administering to said mammal said drug candidate; and analyzing said mammal for development of a disease induced by said disease stimulus. In specific embodiments, the disease stimulus is selected from inoculated tumor cells and inflammation stimuli, said analyzing comprising determining formation of any tumor metastases or determining the level of any inflammatory responses, respectively. In other embodiments, said disease stimulus induces experimental autoimmune encephalomyelitis. In still other embodiments, said disease stimulus induces allergic reactions. The method may comprise comparing the results obtained to corresponding results obtained in a wild type non-human mammal.

BRIEF DESCRIPTION OF THE FIGURES

In the following the invention will be described in greater detail by means of preferred embodiments with reference to the attached figures.

FIG. 6A shows the expression of heparanase, while FIG. 6B shows the expression of MMPs. Decreased levels of MMP-2, MMP-9, MMP-14 mRNA's were noted in cells over-expressing the active form of heparanase, but not the double mutant, inactive form of the enzyme.

DETAILED DESCRIPTION OF THE INVENTION

Figure 1A:
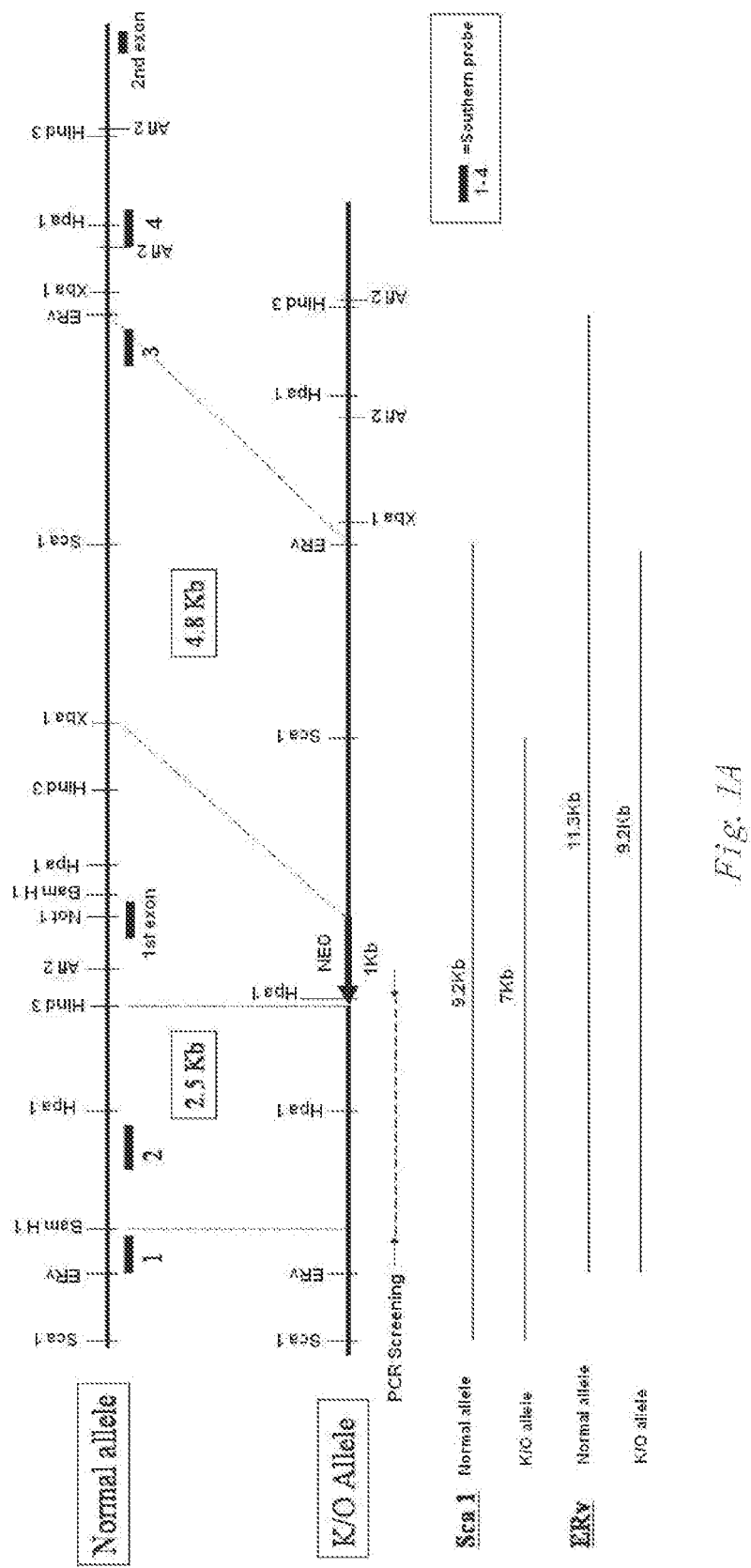
FIG. 1A shows the structure of the 5' end of the heparanase (Hpse) gene (designated as a normal allele) and the targeting construct (designated as a K/O allele) designed for targeted interruption of the Hpse gene. Homologous recombination results in elimination of the first exon and the promoter and replacement with a neo gene. The sizes of the gene products treated with restriction enzymes of Sca I or ERv are indicated. The black bars numbered 1-4 represent probes that can be used for southern blot screening. The orientation of the neo cassette is indicated.

The object of the present invention is to provide transgenic knockout or knockdown cell lines and animals having a disrupted heparanase gene. The disruption results in partial or complete functional inactivation of heparanase gene e.g. by introducing a mutation in the heparanase gene at a location that is crucial for either expression of the gene or production of a functional protein.

Disruption of the heparanase gene may be accomplished by a variety of methods known in the art, such as homologous recombination, mutagenesis, cre/lox technology, antisense technology, and transposon retrotransposon technology.

In homologous recombination, the gene to be knocked out is typically interrupted with a selectable marker, such as antibiotic resistance (e.g. neomycin resistance). Incorporation of the marker into the transcription unit of the target gene disrupts the gene and allows selection of cells that have undergone homologous recombination. One example of many suitable vectors available in the art for use in homologous recombination is Neomycin Selection Cassette (loxP-PGK-gb2-neo-loxP) obtainable from Gene Bridges GmbH.

In one particular embodiment, homologous recombination was used to knock out Hpse gene. To this end, a DNA construct containing a neomycin resistance cassette flanked by DNA having an identical sequence to the targeted Hpse locus was designed and engineered. Non-human mammalian embryonic stem cells were then transfected with a linearized construct, and cells undergone homologous recombination were selected by adding antibiotic to the growth medium. Homologously recombined stem cells were then injected into isolated blastocysts and implanted into pseudo-pregnant non-human mammals. Inactivation of one Hpse allele by homologous recombination was followed by two or more generations of selective breeding to provide homogenous Hpse knockout non-human mammals having both alleles of Hpse gene disrupted.

Accordingly, the present invention provides transgenic non-human mammals including, for example, rodents such as rats, guinea pigs, and especially mice, in which the gene encoding heparanase is disrupted. As a result, such animals lack functional heparanase protein partly or, preferably, completely.

Mouse heparanase gene consists of 12 exons which could be deleted in order to inactivate heparanase. However, some of the exons may be less essential for the activity and their deletion results only in partial inactivation of the heparanase function. Deletions resulting in such incomplete inactivation of heparanase may be called as knockdown deletions. Deleting more than one exon with a single construct is one option in providing Hpse knockout or knockdown animals. The difficulty of the technique, however, increases exponentially with an increase in the length of the sequence to be deleted. Preferred constructs for use in providing Hpse knockout or knockdown mice are ones comprising a deletion of exons 2 and 3, a deletion of exon 4, a deletion of exons 5 to 9, a deletion of exon 10, a deletion of exon 11 or a deletion of exon 12. The most preferred construct comprises a deletion of the promoter and exon 1.

One particular embodiment provides a transgenic Hpse knockout mouse having a mutated Hpse gene with a partly deleted promoter region and a completely deleted exon 1. In a more specific embodiment, the Hpse gene lacks Hind III-Xba I restriction fragment, which fragment in an even more specific embodiment has a nucleotide sequence depicted in SEQ ID NO:1. Such mice are deficient in functional heparanase.

Embodiments of the present invention provide transgenic rats having disrupted Hpse gene and methods for preparation thereof. The strategy of obtaining Hpse knockout or knockdown rats is essentially the same as the one used for targeted gene disruption in mouse. Briefly, the gene coding for heparanase is characterized from a rat genome. Based on the gene structure, a construct designed for deleting a desired part of the gene is established using a suitable plasmid. In a preferred construct, part of the promoter region and exon 1 is deleted. In one particular embodiment, the upstream flanking sequence of 2-3 kb and the down stream (of exon 1) sequence of 4-6 kb is included in the loxp-neo-loxp plasmid for homologue integration. The rat hpse gene contains only 5 exons, and other preferred constructs include ones comprising a deletion of exon 2, a deletion of exon 3, a deletion of exons 2 and 3, a deletion of exon 4 or a deletion of exon 5. The construct may be confirmed by gene-mapping and partial sequencing. The construct is then injected into a rat ES cell, and positive clones are selected based on the selectable marker chosen. The positive clones are screened for homologous integration e.g. by Southern blot analysis and/or PCR. The ES clones with homologous integration are injected into isolated rat blastocysts, which are implanted into pseudo-pregnant rats. Finally, the chimeric offsprings are bred for germ line selection. The heterozygous animals may be inbred to obtain homozygous offsprings.

In another embodiment, transposon retrotransposon technology, such as long interspersed nuclear elements (LINEs) may be used for providing transgenic non-human Hpse knockout mammals, especially rats.

Transgenic knockout or knockdown mammals according to the present invention may be crossed with other transgenic (over-expressing or knockout) non-human mammals to provide further transgenic non-human mammals.

Transgenic non-human mammals according to the present invention may be used to establish heparanase deficient mammalian cell lines. Methods for establishing such cell lines are readily available in the art. Preferred cell lines include embryonic stem cells and fibroblast cell lines. Immortalized fibroblast cell lines are easy to use as a heparanase null cell line.

Success of targeted disruption of Hpse gene may be analyzed by methods known in the art. For example, Northern blotting may be used to confirm down-regulation of heparanase mRNA expression. Other methods are readily available for verifying the elimination of heparanase enzymatic activity.

Transgenic non-human mammals of the invention can be used to screen various drug candidates. The screening method may comprise exposing said mammal to a disease stimulus and administering a drug candidate to said mammal. The mammal is then analyzed for development of a disease induced by the disease stimulus.

In some embodiments, transgenic non-human mammals of the invention can be used to screen, for example, anti-heparanase and/or anti-cancer drug candidates. A typical screening assay comprises inoculating Hpse knockout animals with tumor cells, such as melanoma, carcinoma or hepatoma cells, serving as a disease stimulus. After inoculation, the animals are treated with the test agents, usually by intraperitoneal injection, tail vein injection, oral feeding or nasal intake, at different doses and time-intervals. The effect of administered test agents on formation of tumor metastases, e.g. in lungs or bones, is then evaluated and may be compared to corresponding results obtained with age and sex matched wildtype and/or heparanase over-expressing animals. The assay can be used, for example, to determine effective doses of the test agents.

In transgenic animals of the present invention, lack of heparanase is compensated by up-regulated expression of some MMPs, especially MMP2 and MMP14. Thus, one particular embodiment relates to the use of the animals for evaluating the therapeutic potential of anti-MMP agents, a special class of antimetastatic candidate compounds.

As MMPs are important players in multiple sclerosis and in inflamed or injured central nervous system, one embodiment of the present invention relates to use of Hpse knockout animals to test treatment for multiple sclerosis. To this end, a known disease model, i.e. experimental autoimmune encephalomyelitis, for multiple sclerosis may be used by exposing the transgenic non-human mammals of the invention with Myelin Oligodendrocyte Glycoprotein $(MOG)_{35-65}$ peptide and pertussis toxin (Shao et al., Invest. Ophthalmol. Vis. Sci. 2004, 45: 4060-4065. The effect of administered candidate compound is then evaluated, reduced level of paralysis being indicative of therapeutic potential.

Figure 7:
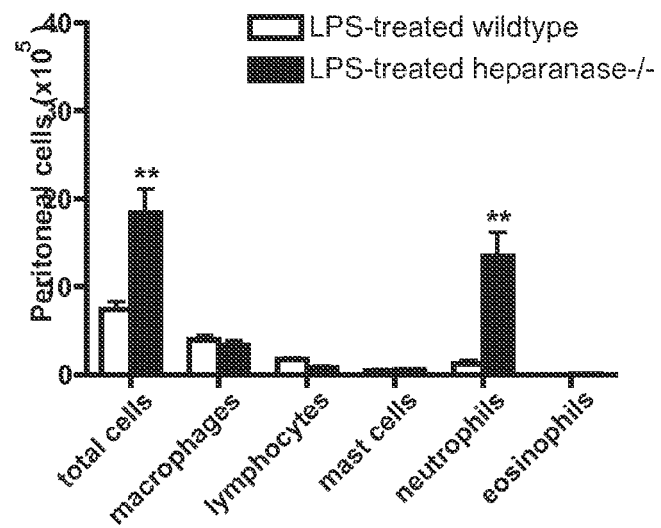
FIG. 7 illustrates increased recruitment of neutrophils in Hpse-KO mice upon lipopolysaccharide (LPS) stimulation. Adult animals (5 in each group) were injected intraperitoneally with 10 µg of LPS dissolved in 100 µl of PBS. After 16 hr, the animals were sacrificed and the peritoneal cavity was flushed with 10 ml of PBS which was collected. The cells were counted and expressed as the total cell number found in the peritoneal cavity.
Figure 8:
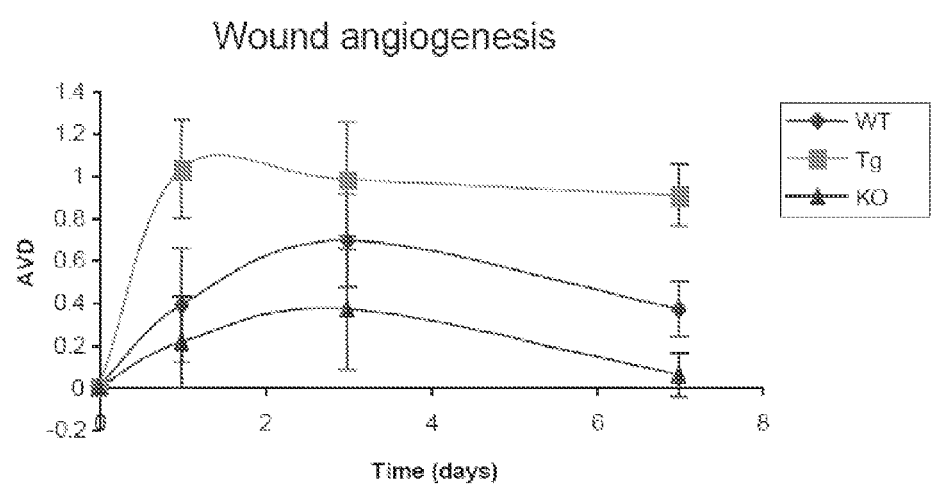
FIG. 8 summarizes the angiogenic response after full dermal incision. Wt, hspe-KO along with hpa-tg mice were anesthetized, shaved, and 1 cm-long, full-thickness incisions were made on the mouse back skin. Incisions were closed by cyanoacrylate glue and examined on days 1, 3, and 7 post wounding by MRI analysis.

Transgenic non-human mammals of the invention show a stronger response to inflammation stimuli as compared to wild type mammals (FIG. 7), and may, therefore, be used to screen anti-inflammatory drug candidates. To this end, Hpse knockout mammals may be challenged with a disease stimulus using one or several of the well-established in vivo inflammation models known in the art including Carrageenan Paw Edema (CPE), Adjuvant-Induced Arthritis (AIA), Collagen-Induced Arthritis (CIA), Mouse Ear Edema, intraperitoneal injection of lipopolysaccharide (LPS) and Air Pouch-cell response analysis in rat or mouse. The effect of administered anti-inflammatory drug candidates is then evaluated, reduced inflammatory response being indicative of anti-inflammatory potential.

Transgenic non-human mammals of the invention may also be used to screen wound-healing agents or drug candidates. In one embodiment, the screening assay comprises anesthetizing and shaving wt and Hpse knockout animals followed by incising back skin of the animals and closing the incisions, typically 1 cm-long full-thickness wounds, by gluing e.g. with a cyanoacrylate glue. Wound healing may be examined by measuring the distance between the epithelial edges for instance on days 1, 3 and 7 post-wounding. Alternatively or in addition, wound fluid may be collected by inserting a suitable sponge, such as a polyvinyl sponge of about 5 mm$^3$, in the wound, and removing the sponge after a desired period of time such as one day. The wound fluid may then be extracted by centrifugation, and the amount of inflammatory factors in the fluid may be analyzed e.g. by Western blotting. The wound tissue may also be subjected to histological analysis after preparation of tissue sections. Such sections may be prepared by fixing the dissected wound tissue e.g. with 4% formaldehyde in PBS, embedding the fixed tissue in paraffin and cutting paraffin sections of about 5 µm. Deparaffinization and rehydration of the paraffin sections may be performed by methods well known in the art prior to histological analysis. The wound-healing drug candidates to be tested in the screening assays may be applied at the wound at any desired time, such as on day 0 or later, or they may be injected subcutaneously.

Furthermore, the transgenic non-human mammals of the invention show increased storage of mast specific proteases. For example, storage of carboxylpeptidase A, mouse mast cell protease-5 and -6 is increased in Hpse knockout mice as demonstrated by Western blot analysis. This finding points to heparanase's role in the regulation of mast cell function, especially in the modulation of allergic reactions. Thus, the present transgenic non-human mammals may be used to screen drug candidates for modulating allergic reactions. The knockout mammals may be challenged to serve as a chronic allergic model. The effects of administered drug candidates on allergic responses are then evaluated and may be compared to corresponding results obtained with age and sex matched wildtype and/or heparanase over-expressing animals.

Transgenic mice according to the present were fertile, exhibited a normal life span and did not show prominent pathological phenotypes, apart of minor alterations (i.e., over branching of mammary glands, enhanced angiogenic response). Histological analysis of various organs such as the brain, heart, liver, lung, kidney and spleen did not show any pathological changes. Thus, knocking out heparanase does not result in animal suffering but provides valuable tools for elaborating the role of heparanase in various physiological and pathological situations, as well as for screening therapeutic drug candidates.

Example 1

Generation of Heparanase Deficient Mice

Heparanase deficient mice were generated through targeted interruption of the gene in ES cells. A targeting vector was constructed to create a functional mutation by deleting the minimal promoter region (about 500 bp upstream of the transcription start point) and the entire first exon (FIG. 1A). Nucleotide sequence of the deleted part is depicted in SEQ ID NO:1. To this end, a 15-kb genomic clone containing the 5' end of the heparanase gene (Hpse) was isolated from a bacteriophage mouse (strain 129/Sv) genomic library (Stratagene, Cedar Creek, Tex.). A 2.5-kb fragment upstream of exon 1 was cloned, as a short homologous arm, into pNT-Lox2 plasmid (kindly provided by Dr. Peter Carmeliet, Department of Molecular and Cellular Medicine, Catholic University, Leuven, Belgium) downstream of the neomycin resistance gene (neo cassette). A 4.8-kb fragment downstream of exon 1 was cloned upstream of the neo cassette as a long homologous arm of the endogenous gene. The targeting vector construct had a total size of about 14.5-kb.

The targeting vector was linearized by the restriction enzyme Not I and electroporated into embryonic stem (ES) cells provided by the Uppsala Transgenic Facility (UUTF). Other ES cells are readily available. Clones expressing the neo-resistant gene were selected by including G418 (350 µg/ml; Invitrogen, Carlsbad, Calif.) in the cell culture medium and analyzed for target gene homologous recombination by Southern blot analysis of genomic DNA. Briefly, genomic DNA extracted from ES cells was digested with either EcoR V or Sca1. The resulting fragments were separated on 0.8% agarose gels and blotted onto a Nylon membrane, followed by hybridization with $^{32}$P-labeled probe #3 shown in FIG. 1A.

In screening 400 neo-resistant ES clones obtained, only two homologous recombinations in the Hpse gene were identified. No additional integration sites were detected in these positive clones. Both positive clones were microinjected into C57BL16 blastocysts, and transplanted into pseudo-pregnant mice yielding chimeric animals, one of which showed germ line transmission. The chimeric male founder mouse was crossed with C57BL16 females. Heterozygous mice were intercrossed to produce Hpse mutant mice. Phenotype studies were performed on mice with a mixed genetic background (129/SvJ/Sv/C57BL/6). Animals were maintained according to the guidelines established by the Swedish and Israeli National Boards for Laboratory Animals.

Figure 1B:
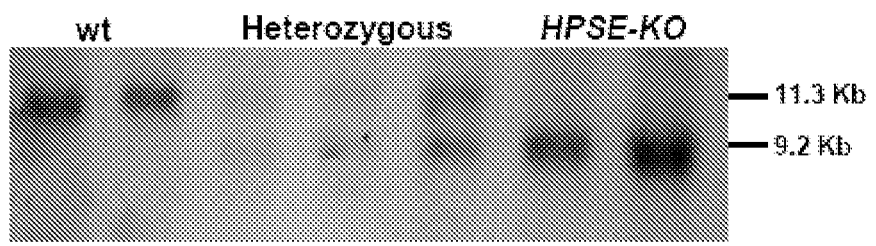
FIG. 1B illustrates a Southern blot analysis of genomic DNA extracted from embryos of the intercross of Hpse+/− heterozygous mice after digestion with ERv. Samples were hybridized with probe 3 as indicated in FIG. 1A. Wildtype (wt) embryos exhibited only the normal allele, heterozygous embryos exhibited both the normal and the mutated allele, and Hpse-KO mice exhibited only the shorter, KO allele.
Figure 1C:
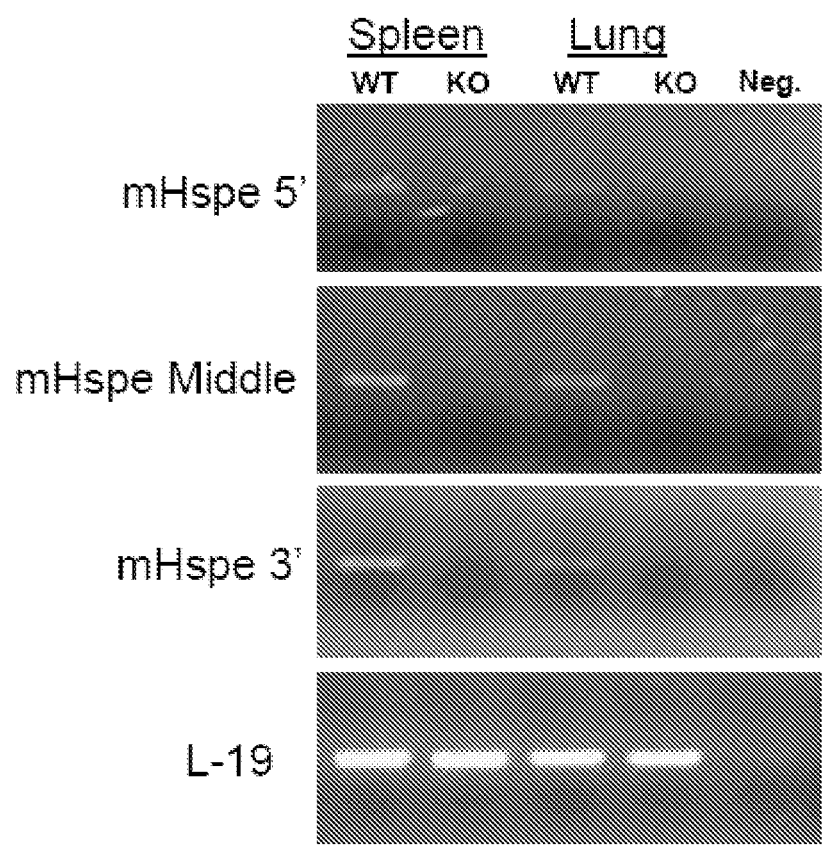
FIG. 1C illustrates PCR analysis of heparanase mRNA expression. RNA was extracted from lungs and spleens of wt and Hpse-KO mice and subjected to PCR amplification using 3 different PCR primer pairs designed to amplify different regions of the Hpse gene as indicated. Heparanase expression was identified in samples derived from wt but not from Hpse- KO. L-19 represents a ribosomal gene used as a housekeeping gene to normalize the mRNA level between different samples.

Genotypic analysis of offsprings from intercrosses between heterozygous littermates was performed by Southern blotting as described above (FIG. 1B), and showed essentially Mendelian heritance, indicating no early embryonic death. To confirm complete interruption of the Hpse gene, the expression of heparanase mRNA derived from different tissues of wt and Hpse-KO mice was examined by real time PCR using specific primers. To this end, total RNA was isolated from about 100 mg spleen or lung tissue using TRIzol (Invitrogen, Carlsbad, Calif.), according to the manufacturers instructions, and quantified by spectrophotometry. After oligo (dT)-primed reverse transcription of 500 ng of total RNA, the resulting single stranded cDNA was amplified using PCR primers. PCR conditions for heparanase were denaturation for 2 min at 94° C. followed by 25 cycles of denaturation for 15 seconds at 94° C., annealing for 1 min at 58° C., and extension for 1 minute at 72° C. Aliquots (10 µl) of the amplified products were separated by electrophoresis on a 1.5% agarose gel and visualized by ethidium bromide staining (Hy Labs, Rehovot, Israel). The primers used for PCR are summarized in Table 1. The primers were designed to amplify the 5', middle, and 3' regions of the heparanase gene. As shown in FIG. 1C, heparanase mRNA was detected only in samples derived from wt mice, but not in samples from the Hpse-KO mice.

TABLE 1

Primers used for detecting Hpse mRNA expression

| Amplified gene/region | | Sequence 5'->3' | SEQ ID NO: |
|---|---|---|---|
| mHpse 5' | forward | 5'-CGACCGACGA CGTGGTAGAC-3' | 2 |
| mHpse 5' | reverse | 5'-GCAACAGCTC CTGGAAGGG-3' | 3 |
| mHpse Middle | forward | 5'-TTTCTGAGCTC TGATGCGCTG-3' | 4 |
| mHpse Middle | reverse | 5'-TGGGCCTTTCA CTCTTGACAG-3' | 5 |
| mHpse 3' | forward | 5'-ACTTGAAGGT ACCGCCTCCG-3' | 6 |
| MHpse 3' | reverse | 5'-GAAGCTCTGG AACTCGGCAA-3' | 7 |
| L-19 | forward | 5'-ATGCCAACTC TCGTCAACAG-3' | 8 |
| L-19 | reverse | 5'-GCGCTTTCGT GCTTCCTT-3' | 9 |

To verify the elimination of heparanase enzymatic activity, 4 blood serum samples and three tissues (liver, kidney and spleen) from wt and Hpse-KO mice were analyzed using sulfate labeled intact ECM (FIG. 1D) or soluble HS side chains (FIG. 1E) as substrates, respectively. Serum samples were diluted 1:1 in reaction buffer (20 mM phosphate-citrate buffer pH 6.2, containing 1 mM dithiothreitol, 1 mM CaCl$_2$, and 50 mM NaCl) and incubated (16 h, 37° C.) on dishes coated with $^{35}$S-labeled ECM. The incubation medium was centrifuged (20,000×g, 4° C., 1 min), and the supernatant containing 35S-labeled HS degradation fragments was analyzed by gel filtration on a Sepharose CL-6B column. Fractions (0.2 mL) were collected and the amount of radioactivity in each fraction was counted in a beta scintillation counter. Nearly intact HS proteoglycans (HSPGs) are eluted from Sepharose 6B just after the void volume (peak I, Kav<0.2), while HS degradation fragments are eluted towards the Vt of the column (peak II, 0.5<kav<0.8). The ECM coated dishes used in the assay were prepared as follows: bovine corneal endothelial cells were cultured in the presence of Na$_2$[$^{35}$S]O$_4$ (GE Healthcare Bioscience, Uppsala, Sweden) added (25 μCi/mL) on days 1 and 5 after seeding, Seven to 10 days later, the cell monolayer was dissolved and the ECM exposed by treating the cell culture dishes with PBS containing 0.5% Triton X-100 and 20 mM NH4OH, followed by four washes with PBS. The ECM remained intact, free of cellular debris and firmly attached to the entire area of the tissue culture dish.

For analysis of the tissue samples, 4 month old wt and Hpse-KO mice were sacrificed, and the organs were immediately homogenized in 2 ml PBS, pH 7.4, containing 1% Triton X-100 and a protease inhibitor cocktail (Sigma-Aldrich, St. Louis, Mo.). The homogenates were incubated on ice for 30 min followed by centrifugation at 4° C., 15,000 rpm for 20 min. The supernatant was loaded onto a HiTrap heparin-Sepharose (GE Healthcare Bioscience) column equilibrated in the homogenization buffer. After washing with 10 ml PBS, the bound material was eluted with PBS containing 1M NaCl. The total amount of protein was determined by the Bradford method. Samples of 50 μg protein from the elution were incubated (37° C., overnight) with 5,000 cpm [$^3$H]acetyl-labeled HS in 20 mM phosphate-citrate buffer, pH 5.8, 1 mM dithiothreitol, 1 mM CaCl$_2$, and 50 mM NaCl. The resulted products were analyzed by gel chromatography on Superose-12 column (GE Healthcare Biosciences).

Figure 1D:
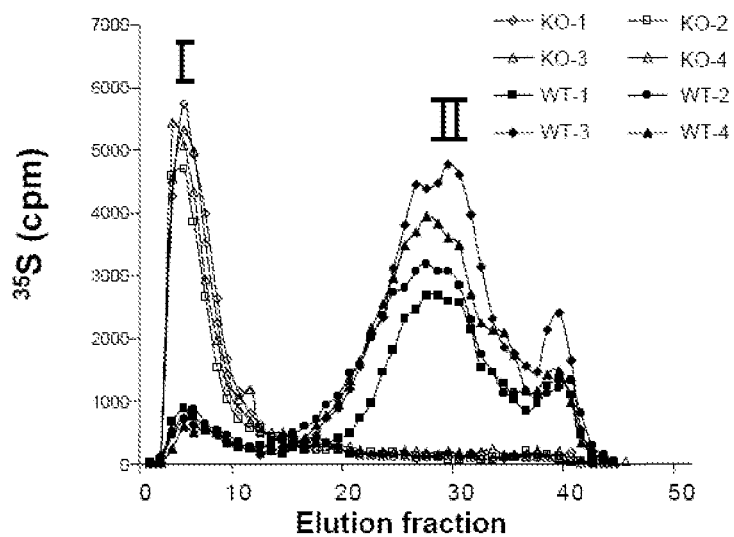
FIG. 1D illustrates heparanase activity assay. Blood samples derived from 4 wt and 4 Hpse-KO mice were incubated (16 h, 37° C., pH 6.2) with sulfate labeled ECM. Labeled degradation products released into the incubation medium were subjected to gel filtration analysis on Sepharose 6B. High heparanase activity was noted only in samples derived from wt mice; no heparanase activity was detected in Hpse-KO samples.
Figure 1E:
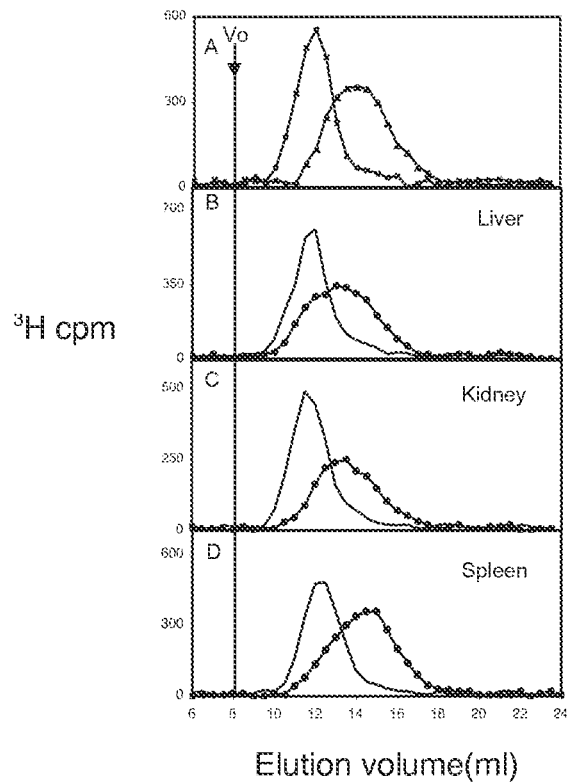
FIG. 1E illustrates HS degradation assay. Liver, kidney and spleen tissue extracts derived from wt and Hpse-KO mice were homogenized and incubated (18 h, 37° C., pH 5.8) with $^3$H-acetyl labeled HS. The reaction mixture was then subjected to gel chromatography on Superose-12. The upper panel shows blank (peak I) and positive control (recombinant heparanase; peak II) incubations. Incubations of Hpse-KO tissue extracts (line) resulted in a same elution profile as the blank incubation (upper panel), indicating no detectable heparanase activity; while the incubations with wt tissue extracts resulted in substantial cleavage of the HS substrate (dotted line), as that of the incubation with recombinant heparanase (upper panel).

Regardless of the assay system, none of the samples from Hpse-KO mice showed heparanase activity, while the wt samples exhibited normal levels of heparanase activity (FIGS. 1D and E). Of particular significance is the lack of heparanase activity in serum samples containing activated platelets and white blood cells known to express exceedingly high levels of the enzyme. As demonstrated in FIG. 1D, blood samples derived from wt mice exhibited high levels of heparanase activity, as detected by the large amount of low molecular weight material eluted in fractions 20-40 (FIG. 1D, peak II). Labelled fragments eluted in peak II were shown to be degradation products of HS, as they were 5-6 fold smaller than intact HS chains of HSPGs, resistant to further digestion with papain and chondroitinase ABC, and susceptible to deamination by nitrous acid. In contrast, blood samples derived from Hpse-KO mice exhibited no heparanase activity as revealed by the lack of HS degradation fragments (peak II) and the generation of high molecular weight material eluted in fractions 5-10 (peak I, FIG. 1D). This material, representing nearly intact HSPGs, is produced by proteolytic degradation of the proteoglycan core protein by proteases residing in the ECM and cell lysate. Similarly, there was no cleavage of $^3$H-labeled HS upon incubation with extracts of liver, kidney and spleen derived from Hpse-KO mice (peak I) vs. a significant degradation of HS upon incubation with the corresponding wt tissue extracts (peak II, FIG. 1E). Altogether, these data clearly demonstrate complete elimination of heparanase enzymatic activity in the Hpse-KO mice.

Example 2

Phenotypic Analysis of Heparanase Deficient Mice

The homozygous mutant animals showed no obvious aberrant phenotype, were fertile and exhibited a normal life span. To examine any possible age-related phenotypes, 6, 12- and 18-month old mice were sacrificed and organs were dissected and fixed in a solution containing 96% ethanol, 1% glacial acetic acid and 3% distilled water. Paraffin embedded tissue sections were stained with hematoxilin and eosin. Histological examination of the sections derived from the brain, heart, liver, lung, kidney and spleen did not reveal significant structural or pathological abnormalities in the Hpse-KO mice.

Figure 3:
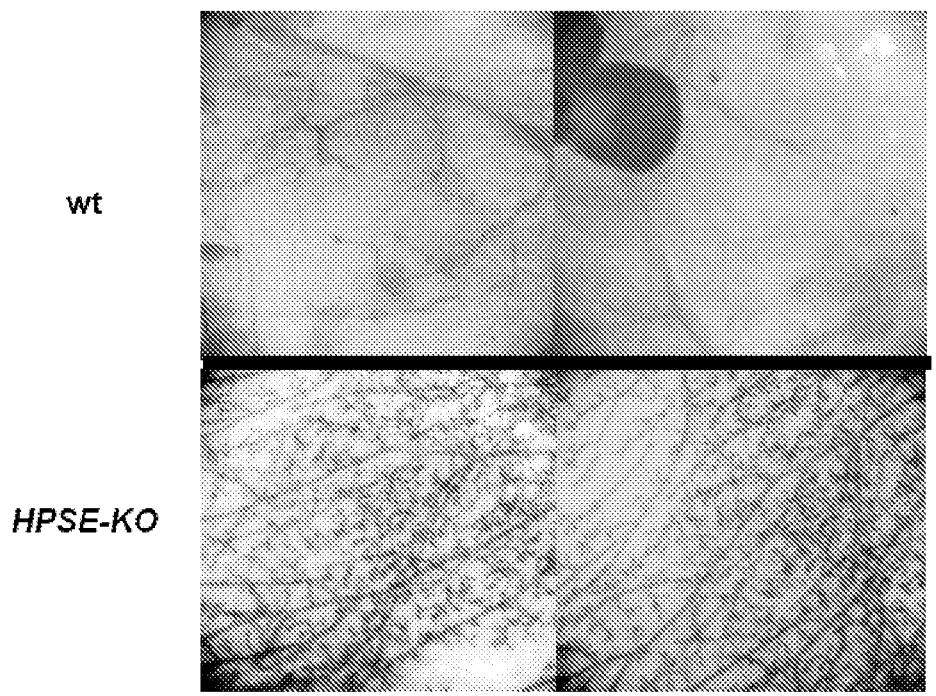
FIG. 3 illustrates the morphological appearance of mammary glands from wt vs. Hpse-KO mice. Whole-mount preparations of mammary glands from 3-month-old virgin mice were stained with hematoxylin. Hpse-KO derived mammary glands (bottom panels) showed abundant side branches and alveolar structures compared with glands from age-matched wt animals (upper panels).

To study mammary gland morphogenesis, whole-mount mammary glands derived from 3-month old virgin homozygous Hpse-KO or wt mice were prepared as known in the art and fixed in Tellys fixative (100 ml EtOH 70%, 5 ml formalin, 5 ml glacial acetic acid), rehydrated and stained with hematoxylin for 3 h. After staining, the glands were washed in tap water (1 h), dehydrated and stored in methyl salicylate. Surprisingly, virgin Hpse-KO mice exhibited abnormal abundant branching of ducts in the mammary gland and precocious alveolar structures, typical of pregnant mice (FIG. 3, lower panels), whereas virgin wt virgin mice exhibited poorly developed mammary glands (FIG. 3, upper panels). Previously, transgenic virgin mice over-expressing the human heparanase gene (hpa-t1 mice) have been reported to exhibit similar mammary gland morphology as the virgin homozygous Hpse-KO mice. However, unlike the hpa-t1 vs. control mice, there was no significant difference between the wt and Hpse-KO mice in the width of the primary ducts.

To examine the role of heparanase and effect of HS structural alternations on liver and kidney function, blood samples were taken from 15 wt and 15 Hpse-KO mice, before and after a 72 h fasting. Samples were analysed for total protein and contents of creatinine, aspartate aminotransferase (AST), alanine aminotransferase (ALT), and alkaline phosphatase (ALP). To this end, urine samples (25 μl) were analyzed for total protein and creatinine content, using an automated Kodak 250 system. Blood samples (25 μl) were examined for creatinine, aspartate aminotransferase (AST), alanine aminotransferase (ALT), and alkaline phosphatase (ALP) content, using an automated Kodak 950 system. No significant differences between wt and Hpse-KO mice were detected, both before and after fasting. Furthermore, since platelets contain high amount of heparanase, blood samples were also examined for coagulation properties (i.e., APTT). Again, there was no significant difference between the Hpse-KO and wt mice.

Previously, it has been reported that heparanase is more readily expressed during liver development and regeneration as compared to mature healthy liver. Moreover, the present inventors have found out that treatment with recombinant active heparanase promotes liver regeneration (unpublished results). It was thus assumed that the liver of Hpse-KO mice may exhibit a slower regeneration rate in response to partial hepatectomy. Wt and Hpse-KO mice (4 animals in each group) were subjected to partial hepatectomy and examined every other day for liver regeneration applying MRI to evaluate the liver size in vivo. Unexpectedly, no significant difference was observed between the two groups during 8 days post hepatectomy.

Example 3

Biochemical Analysis of Heparan Sulfate Structure in Heparanase Deficient Mice

As degradation of heparin sulfate (HS) is one main function of heparanase, HS derived from selected organs was analyzed. For this purpose, wild type and Hpse-KO mice were injected intra-peritoneally with 0.5 mCi $Na_2^{35}SO_4$ (specific activity 1,500 Ci/mmol; Perkin Elmer, Waltham, Mass.) and maintained for 45 min with free access to water and food. The animals were then sacrificed by cervical dislocation and the organs were dissected. The tissues were homogenized with a Dounce homogenizer in 6 volumes of ice-cold 50 mM Tris-HCl, pH 7.4, 1% (v/v) Triton X-100, 4 M urea, 0.25 M NaCl containing a protease inhibitor cocktail (Sigma-Aldrich), followed by incubation at 4° C. overnight. Following centrifugation, the supernatants were applied to DEAE-Sephacel columns equilibrated in 50 mM Tris-HCl, pH 7.4, 0.3 M NaCl. The columns were extensively washed with the same buffer and were then eluted with the same buffer containing 1.5 M NaCl. Eluates were desalted, lyophilized and digested with chondroitinase ABC (Seikagaku, Tokyo, Japan) and benzonase (Merck, San Diego, Calif.). The digests were then re-applied to DEAE-Sephacel to remove degraded chondroitin sulfate and oligonucleotides. The HSPG fractions eluted with 1.5 M NaCl were pooled for further analysis.

For analysis of HS molecular structure, gel chromatography of HSPGs and HS free chains was preformed on a Superose 12 column eluted with 50 mM Tris-HCl, pH 7.4, 1 M NaCl, 0.1% Triton X-100. To analyze domain organization, HS samples were subjected to cleavage at N-sulfated GlcN residues by treatment with nitrous acid at pH 1.5, followed by reduction with $NaB[^3H]_4$. The reduced products were separated by gel chromatography on a column (1×200 cm) of Bio-Gel P-10 (Bio-Rad, Hercules, Calif.) in 0.5 M NaCl. A portion of the nitrous acid degradation products was applied to a Sephadex G-15 column and disaccharides were recovered. After desalting and concentration, the $^3H$ or $^{35}S$ labeled disaccharides, derived from N-sulfated domains, were further analyzed by anion-exchange HPLC on a Partisil-10 SAX column, as known in the art.

Figure 2:
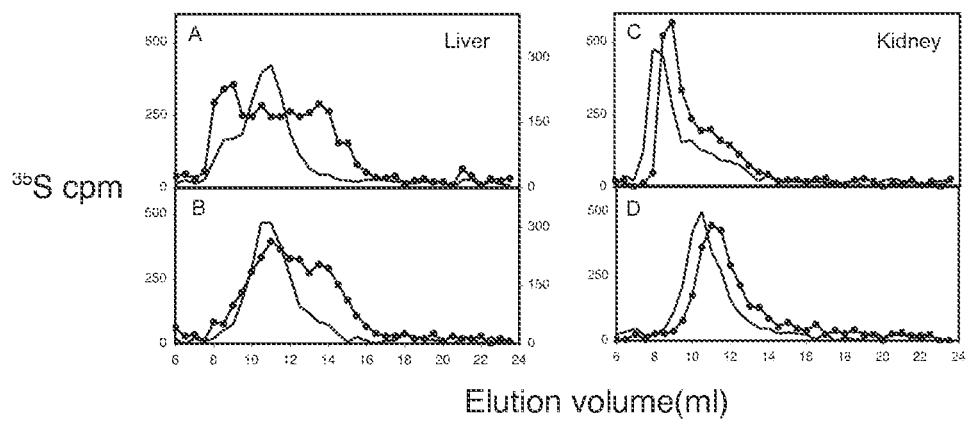
FIG. 2 illustrates the molecular structure of HS from wt (dotted line) vs. Hpse-KO mice (continuous line). Total metabolically $^{35}$S-labeled HS chains from liver (panels A and B) and kidney (panels C and D) were analyzed on Superose 12 column. Panels A and C show the molecular structure of HSPGs, while panels B and D show the molecular structure of free HS chains.

As expected, HS chains from Hpse-KO tissues were of higher molecular mass in comparison to HS extracted from wt tissues (FIG. 2). In addition, the elution peaks of free HS chains isolated from Hpse-KO tissues appeared narrower and more symmetrical, indicating less heterogeneity in size distribution in comparison with the elution profile of HS side chains isolated from wt tissues (the overall broad size of peaks reflects the state of HS biosynthesis). Structural analysis of HS sulfation and disaccharide composition did not show a detectable difference between samples derived from wt and Hpse-KO tissue.

Example 4

Analysis of Endothelial Sprouting and Angiogenesis in Heparanase Deficient Mice

Figure 4A:
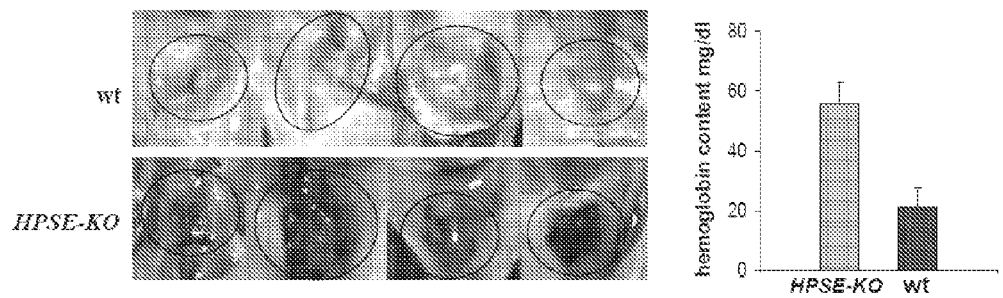
FIG. 4A illustrates growth factor induced endothelial sprouting in an aortic ring model. Aortic rings derived from Hpse-KO and wt mice were subjected to FGF-2 induced vascular sprouting for 6 days. The rings were then fixed, stained with 0.02% crystal violet solution and evaluated for vascular sprouting. A more extensive endothelial sprouting was noted in Hpse-KO derived rings (lower panels) as compared to wt derived rings (upper panels).

The involvement of heparanase in cell migration and angiogenesis is well documented. Therefore, the effect of heparanase knockout on endothelial cell migration and sprouting was evaluated. First, an ex vivo aortic ring assay was applied. Briefly, 8 wt and 8 Hpse-KO mice were sacrificed and their aortas were cleaned and cut into 1-2 mm thick rings. The rings were embedded in 3-dimensional growth factor-depleted Matrigel (BD Biosciences, San Jose, Calif.), and incubated in 0.5 ml Bio-MPM (Biological industries, Beit haemek, Israel) in the absence or presence of added FGF-2 (50 ng/mL). The rings were maintained for 6 days (37° C., 8% $CO_2$, humidified atmosphere), and both the medium, and FGF-2 were replaced every 2 days. Vascular sprouting was evaluated every day for a period of 6 days, then fixed with 4% formalin for 24 h and stained with 0.02% crystal violet in ethanol (Sigma-Aldrich), and photographed using a Nikon Eclipse TS 100 phase-contrast microscope. As expected, in the absence of FGF-2 there was little or no sprouting in either the wt or Hpse-KO rings (not shown). Upon stimulation with FGF-2, both wt and Hpse-KO rings showed endothelial sprouting (FIG. 4A). Notably, Hpse-KO derived rings exhibited a more pronounced tube formation (FIG. 4A, lower panels) compared to wt aortic rings (FIG. 4A, upper panels), suggesting an increased response to FGF-2 stimulation.

Figure 4B:
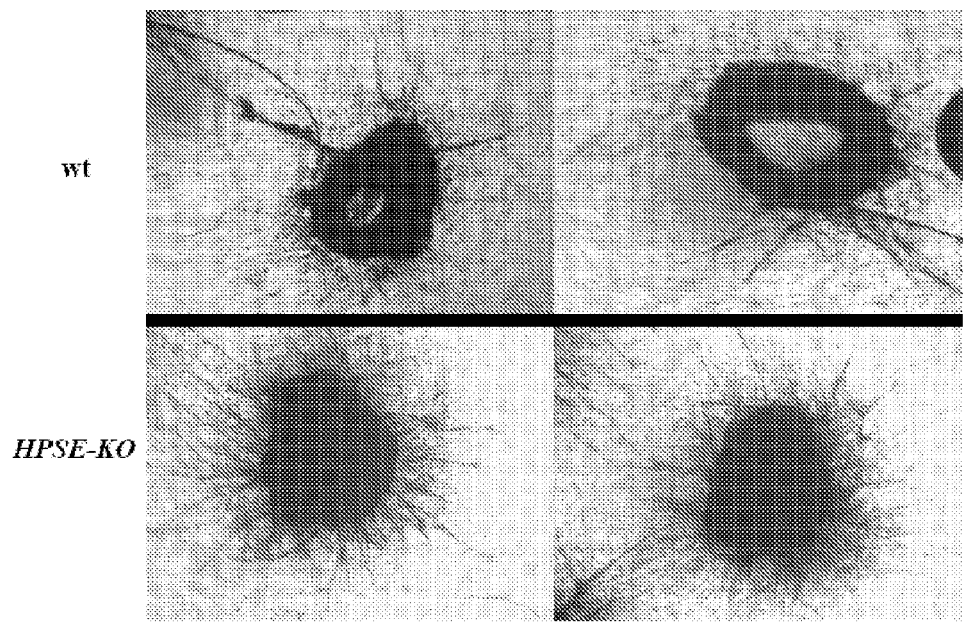
FIG. 4B illustrates angiogenesis in a Matrigel plug assay. Hpse-KO (lower panels) and wt (upper panels) mice were injected subcutaneously with 200 µl of growth factor depleted Matrigel supplemented with FGF-2 (80 ng/ml). Seven days later, the Matrigel plugs were excised and photographed, homogenized and evaluated for hemoglobin content using Drabkin's reagent. A pronounced angiogenic response was noted in Hpse-KO vs. wt mice (55.57±7.18 mg/dl vs 26±4.8 mg/dl; p=0.0002, respectively).

To validate the ex vivo results, we performed an in vivo angiogenesis assay. In this model, mice were injected subcutaneously with 200 μL of growth factor depleted Matrigel with or without FGF-2 (80 ng/mL). Seven days later, the Matrigel plugs were excised, photographed, homogenized in a hypotonic lysis buffer (250 μl of 0.1% Brij-35/plug) and centrifuged for 5 min at 5,000 g. The supernatant was used in duplicates to evaluate neovascularization by measuring the content of hemoglobin with Drabkin's reagent. A profound angiogenic response was induced by Matrigel-embedded FGF-2 in the Hpse-KO mice compared with wt mice (FIG. 4B), corroborating the ex vivo results. Determination of hemoglobin revealed a ~2-fold increase in the hemoglobin content of Matrigel plugs embedded in Hpse-KO compared to wt mice (55.57±7.18 mg/dl vs. 26±4.8 mg/dl; p=0.0002, respectively).

Example 5

Analysis of Compensatory Responses in Heparanase Deficient Mice

The unexpected result of abnormal mammary gland morphology and increased neovascularization in Hpse-KO mice led to the investigation of the mechanism behind this phenotype. One question was whether other ECM degrading enzyme(s) were compensating for the lack of heparanase expression. Hpa2, a gene exhibiting significant homology (~38%) to the heparanase gene (disclosed in WO 01/77341), but lacking any detectable heparanase enzymatic activity, was the first candidate to examine. Analysis of Hpa2 expression did not reveal any difference between the wt and Hpse-KO mice. Furthermore, the increased HS length found in Hpse-KO mice does not point to an additional heparanase-like enzyme.

Taking into account that matrix metalloproteinases (MMPs) play important roles in rearranging the ECM structure and thereby in tissue remodeling, morphogenesis and neovascularization, the expression of MMPs was investigated by real-time PCR. For this purpose, total RNA extracted from the kidney, liver and mammary gland of Hpse-KO and wt mice, was analyzed using specific primers corresponding to MMP-2, -3, -9, -14 and -25 (Table 2). Real-time quantitative PCR analysis was performed with an automated rotor gene system RG-3000A (Corbett research, Sydney, Australia). The PCR reaction mix (20 µl) was composed of 10 µl QPCR SYBR green mix (ABgene, Epsom, UK), 5 µl of diluted cDNA (each sample in a six-plicate) and a final concentration of 0.3 µM of each primer. PCR conditions were as follows: an initial denaturation step at 95° C. for 15 min; 40 cycles of denaturation at 94° C. for 15 s, hybridization at 57° C. for 30 s, and elongation at 72° C. for 30 s. Actin primers were used as an internal standard.

TABLE 2

Primers used for detecting MMP expression

| Target | Orientation | Sequence 5'->3' | SEQ ID NO: |
|---|---|---|---|
| MMP2 | forward | 5'-AGC GTG AAG TTT GGA AGC AT-3' | 10 |
| MMP2 | reverse | 5'-CAC ATC CTT CAC CTG GTG TG-3' | 11 |
| MMP9 | forward | 5'-AGA CGA CAT AGA CGG CAT CC-3' | 12 |
| MMP9 | reverse | 5'-GTG GTT CAG TTG TGG TGG TG-3' | 13 |
| MMP14 | forward | 5'-GCC TGG AAC ATT CTA ACG A-3' | 14 |
| MMP14 | reverse | 5'-CTT TGT GGG TGA CCC TGA CT-3' | 15 |
| MMP25 | forward | 5'-GCT GAC TCG CTA TGG CTA CC-3' | 16 |
| MMP25 | reverse | 5'-GTC ATT GGG TCC ATT TGT CC-3' | 17 |
| Actin | forward | 5'-ATG CTC CCC GGG CTG TAT-3' | 18 |
| Actin | reverse | 5'-CATAGGAGTCCT TCTGACCCATTC-3' | 19 |

Figure 5A:
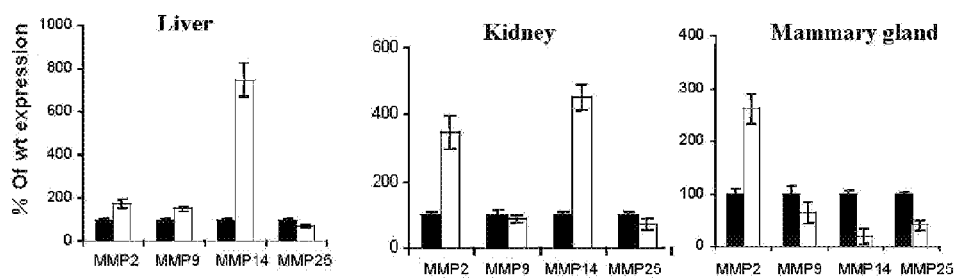
FIG. 5A illustrates MMP expression in Hpse-KO mice assessed by real-time PCR. RNA was extracted from kidney, liver and mammary glands of wt and Hpse-KO mice and subjected to quantitative real time PCR analysis to evaluate the expression of MMP-2, MMP-9, MMP-14 and MMP-25. The expression level determined for each MMP in the wt tissue (white bars) was regarded as 100% and the corresponding expression determined in the Hpse-KO tissue (black bars) mice are presented as percentage relative to it. Each reaction was repeated 6 times and the mean±SD is indicated.

The expression level of different MMPs in the wt tissue was regarded as 100%, and the MMP levels in the Hpse-KO mice were calculated relative to this value. The results (FIG. 5A) indicated that lack of heparanase expression was associated with marked changes in the expression levels of several members of the MMP family. MMP-2 was over-expressed (2-3.5 fold) in all samples extracted from Hpse-KO vs. wt mice. MMP-14 was over-expressed (4-7 fold) in the liver and kidney, but was down regulated (~4 fold) in mammary glands derived from Hpse-KO vs. wt mice. MMP-9 and MMP-25 expression levels were altered as well, depending on the tissue (FIG. 5A).

Figure 5B:
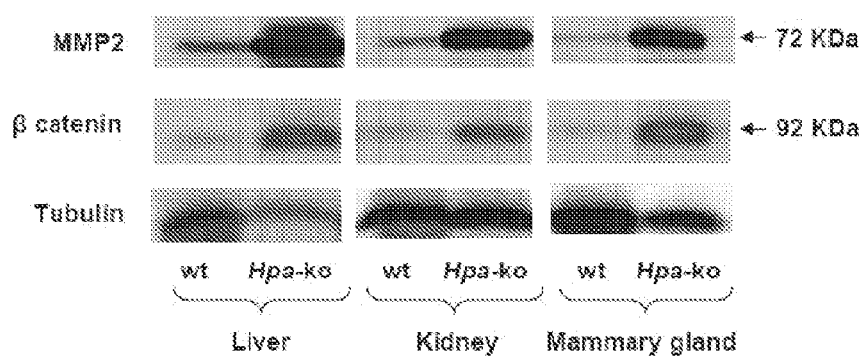
FIG. 5B illustrates MMP expression in Hpse-KO mice as determined by Western blot analysis. Liver, kidney and mammary gland tissue extracts were subjected to Western blot analysis using anti-mouse MMP-2 monoclonal antibodies (mA801B; upper panels), anti mouse β-catenin (mAb610154; middle panels), or anti mouse a-tubulin (B-5-1-2; lower panels).

These results were further corroborated by Western blot analysis revealing increased levels of the MMP-2 protein in homogenized tissues extracted from the liver, kidney and mammary glands of Hpse-KO vs. wt mice (FIG. 5B upper panels). Aliquots of tissue extracts (50 µg) were separated by electrophoresis in 10% SDS-polyacrylamide gel (PAGE) and transferred to Immobilon-P membrane (Millipore, Bedford, Mass.). MMP2 was detected by anti-mouse MMP2 monoclonal antibodies 801B (1:150, kindly provided by Dr. Rafael Fridman, Wayne State University, Detroit, Mich.). β-catenin was detected by anti-mouse monoclonal antibody (1:150, BD transduction laboratories, San Jose, Calif.), and anti mouse a-tubulin clone B-5-1-2 (1:5000; sigma). Membranes were incubated with primary antibodies for 2 h at room temperature, washed in TTBS and probed with HRP-conjugated secondary antibody (Jackson Laboratories, Bar Harbor, Me.). After several washes in TTBS, detection of the secondary antibodies was performed using the SuperSignal Chemiluminescent Substrate system (Pierce, Rockford, Ill.). The chemical illumination signals were exposed to Fuji medical X-ray film (Super RX).

It was further investigated whether the increased expression of MMP-2 is manifested by elevated MMP-2 enzymatic activity, as well. For this purpose, plasma samples derived from wt and Hpse-KO blood were subjected to zymography and evaluated for MMP-2 activity. MMP-2 activity was 2 fold higher in plasma samples derived from Hpse-KO vs. wt mice.

Figure 5C:
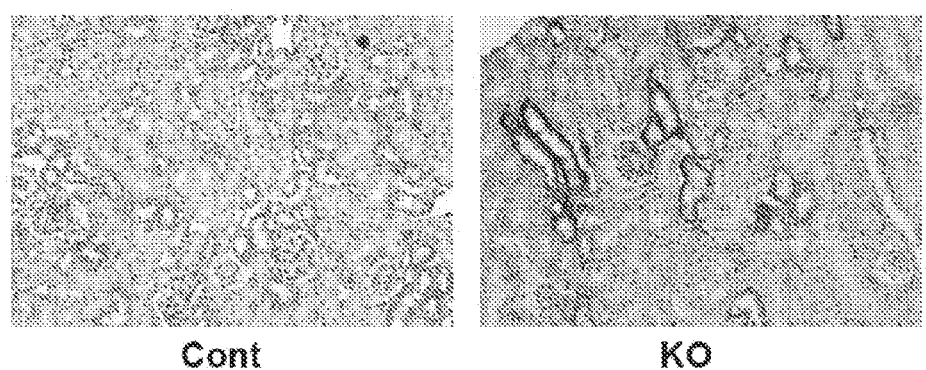
FIG. 5C shows β-catenin immunostaining. Paraffin embedded kidney samples were subjected to immunostaining using an antibody directed against β-catenin. Increased staining was observed in kidney section derived from Hpse-KO compared to that from wt.

Next, a possible molecular pathway involved in the interaction between heparanase and MMPs was elaborated. Since β-catenin was previously implicated in MMP regulation, its activation was evaluated by examining β-catenin accumulation in the cytoplasm. Western blot analysis of tissue extracts revealed accumulation of β-catenin in the liver, kidney and mammary glands derived from Hpse-KO compared to wt mice (FIG. 5B, middle panel). Similarly, immunostaining of kidney tissue sections derived from wt and Hpse-KO mice (FIG. 5C) revealed increased β-catenin staining in Hpse-KO kidneys, corroborating the Western blot results.

Furthermore, the inter relation between heparanase and MMPs was investigated by transfecting human breast carcinoma MDA-231 cells, normally expressing moderate levels of heparanase, with either active or mutant heparanase (active site Gin 225 and Gin 343 replaced by Ala) lacking enzymatic activity. mRNA expression levels were determined by real-time PCR using primers shown in Table 3.

TABLE 3

Primers used for detecting mRNA expression of transfected breast cancer cells

| Target | Orientation | Sequence 5'->3' | SEQ ID NO: |
|---|---|---|---|
| Hpse | forward | TACCTTCATTGCACAAACACTG | 20 |
| Hpse | reverse | ACTTGGTGACATTATGGAGGTT | 21 |
| MMP2 | forward | GCGGCGGTCACAGCTACTT | 22 |
| MMP2 | reverse | CACGCTCTTCAGACTTTGGTTCT | 23 |
| MMP9 | forward | CCTGGAGACCTGAGAACCAATC | 24 |

TABLE 3-continued

Primers used for detecting mRNA expression
of transfected breast cancer cells

| Target | Orientation | Sequence 5'->3' | SEQ ID NO: |
|---|---|---|---|
| MMP9 | reverse | CCACCCGAGTGTAACCATAGC | 25 |
| MMP14 | forward | CGCTACGCCATCCAGGGTCTCAAA | 26 |
| MMP14 | reverse | CGGTCATCATCGGGCAGCACAAAA | 27 |
| MMP25 | forward | AGTTGCTGTCCAGCCTCAGT | 28 |
| MMP25 | reverse | CCAAAGTCTCCTGCCTTCTG | 29 |

Figure 6:
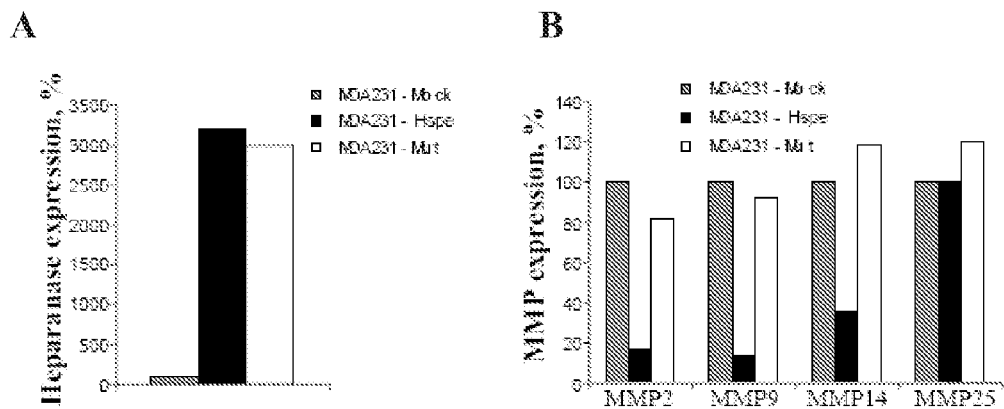
FIG. 6 illustrates expression of MMPs in heparanase transfected MDA-231 human breast carcinoma cells. MDA-231 cells were transfected with a mock (empty vector) or either active or mutated inactive heparanase gene. mRNA expression levels were determined by real-time PCR. The expression levels determined in the mock transfected cells were regarded as 100%, and the levels in Hpse and mut-Hpse transfected cells were presented as percentage relative to the mock transfected cells.

Both the active and inactive mutant heparanase were 30 fold over-expressed in the Hpse-transfected cells as compared to mock transfected cells (FIG. 6A). As demonstrated in FIG. 6B, cells transfected with active heparanase exhibited a marked decrease in the expression of MMP-2 (5.8 fold), MMP-9 (6.5 fold) and MMP-14 (3 fold), a mirror image of the increased expression found in Hpse-KO mice. In contrast, transfecting the MDA-231 cells with mutant inactive heparanase did not affect MMP expression (FIG. 6B), indicating that heparanase enzymatic activity is involved in the observed regulation of MMP expression.

Example 6

Heparanase Deficient Mice as a Model for Evaluation of Candidate Compounds for Treating Multiple Sclerosis Experimental autoimmune encephalomyelitis (EAE) is induced in optimally 6 to 8 weeks old Hpse-KO female mice on C57/BI genetic background by the following scheme:

Day 0: S.c. injection of 300 µg $MOG_{35-55}$ peptide in 50:50 emulsion with Complete Freunds Adjuvant; 200 µl injection volume;

I.p. injection of 500 mg Pertussis Toxin; injection volume 100 ml;

Day 2: I.p. injection of 500 µg Pertussis Toxin; injection volume 100 µl;

Day 7: S.c. injection of 300 µg $MOG_{35-55}$ in 50:50 emulsion with Complete Freunds Adjuvant; 200 µl injection volume.

On day 0 or earlier, the mice are marked or tagged for later identification in a blind test study. Furthermore, the mice are weighed and health status checked prior to initiation of the study.

The mice are checked daily and from day 7 (or earlier) onwards (at maximum until day 28) the mice are weighed and monitored to get a clinical score (c.s.) every day.

| c.s. | Description of symptoms |
|---|---|
| 0 | Healthy |
| 0+ | General condition affected in any way, however not necessarily due to EAE |
| 1 | Weak tail/part of tail paralyzed |
| 2 | Severe paralysis of tail |
| 3 | Altered, but not well defined, movements in hind (or sometimes front) limbs and/or lowered crupa, often unwilling to move on grid |
| 4 | Well defined alteration of movements in hind (or sometimes front) limbs (e.g. limping and/or frequent slipping when walking on grid and/or slight wobbling). Often unwilling to move on grid. Walks quite well on flat surface, sometimes hesitating. |
| 5 | Wobbling and/or strong limping in hind (or sometimes front) limbs, slips on grid. Often weak crupa. Often unwilling to move on grid. Hesitating movements on flat surface with lowered back and hind legs slipping outwards. |
| 6 | Slow, dragging movements of hind limbs. Weak crupa. |
| 7 | Very weak hindlegs, retained toe reflexes, sometimes making walking movements. |
| 8 | Paralyzed hind legs, very weak/paralyzed crupa. |
| 9 | Paralyzed hind legs, paralysis far above crupa. |

The test compounds may be applied e.g. on day 0, 7 or later, and the clinical scores as indicated in the above table are evaluated. The lower the clinical score, the higher the therapeutic potential of the test compound.

The invention claimed is:

1. A heparanase activity-eliminated transgenic mouse having a disrupted heparanase gene, wherein said disrupted heparanase gene lacks a HindIII-XbaI fragment comprising part of the promoter and exon1, and the transgenic mouse is homozygous for disruption of heparanse gene.

2. An isolated cell derived from a transgenic mouse according to claim 1.

3. A method of making a transgenic mouse, comprising:
   a) deleting part of the heparanase gene by homologous recombination in mouse embryonic stem cells, wherein the deleted part is the HindIII-XbaI fragment comprising part of the promoter and exon 1;
   b) introducing recombinant cells obtained in step a) into an isolated blastocyst;
   c) transplanting said blastocyst into a pseudopregnant mouse;
   d) allowing said transplanted blastocyst to develop into a transgenic mouse;
   e) breeding said transgenic mouse to produce offspring; and
   f) screening said offspring to identify a heparanase activity-eliminated transgenic mouse.

4. The method according to claim 3, wherein a nucleotide sequence of the deleted part in a) is depicted in SEQ ID NO: 1.

5. A vector for making a transgenic mouse according to claim 1, said vector comprising a nucleic acid sequence encoding a heparanase knockout construct, wherein a part of the heparanase coding sequence is replaced with a selectable marker sequence, wherein said part is the HindIII-XbaI fragment comprising part of the promoter and exon 1.

6. The vector according to claim 5, wherein said selectable marker sequence comprises a neomycin resistance gene.

7. A method of screening a therapeutic drug candidate, comprising
   a) providing a transgenic mouse according to claim 1;
   b) exposing said mouse to a disease stimulus
   c) administering to said mouse said drug candidate; and
   d) analyzing said mouse for development of a disease induced by said disease stimulus.

8. The method according to claim 7, wherein said disease stimulus comprises inoculated tumor cells, and said step d) comprises determining formation of any tumor metastases.

9. The method according to claim 7, wherein said disease stimulus is an inflammation stimulus, and said step d) comprises determining the level of any inflammatory responses.

10. The method according to claim 7, wherein said disease stimulus induces experimental autoimmune encephalomyelitis.

11. The method according to claim 7, wherein said disease stimulus induces an allergic reaction.

12. The method according to any one of claims 7-11, further comprising comparing the results obtained to corresponding results obtained in a wild type mouse.

\* \* \* \* \*